United States Patent
Lopez Cabrera et al.

(10) Patent No.: US 6,793,932 B2
(45) Date of Patent: Sep. 21, 2004

(54) PREPARATION FOR VETERINARY USE

(75) Inventors: Antonio Lopez Cabrera, Barcelona (ES); Josep Homedes Beguer, Barcelona (ES)

(73) Assignee: Laboratories Del Dr. Esteve, S.A., Barcelona (ES)

( * ) Notice: Subject to any disclaimer, the term of this patent is extended or adjusted under 35 U.S.C. 154(b) by 193 days.

(21) Appl. No.: 10/043,168

(22) Filed: Jan. 14, 2002

(65) Prior Publication Data

US 2003/0068294 A1 Apr. 10, 2003

(30) Foreign Application Priority Data

Feb. 6, 2001 (ES) .......................................... P200100254

(51) Int. Cl.⁷ .......................... A61K 11/00; A01N 25/32
(52) U.S. Cl. ....................... 424/437; 424/405; 424/406; 424/407; 424/725; 424/729; 424/762; 424/764; 514/159; 514/578; 514/560

(58) Field of Search ................................. 424/438, 405, 424/406, 407, 437, 401, 725, 758, 729, 762, 764, 578, 560; 514/159, 160, 163–165, 724, 553, 557, 578, 818, 922, 558

(56) References Cited

U.S. PATENT DOCUMENTS 5,034,221 A * 7/1991 Rosen et al. ................... 424/73
5,747,021 A * 5/1998 McKenzie et al. ............. 424/73
6,503,488 B1 * 1/2003 Rosen et al. ................... 424/65

OTHER PUBLICATIONS

Martindale—The Extra Pharmacopoeia pp. 183, 256–260.*

* cited by examiner

*Primary Examiner*—Neil S. Levy
(74) *Attorney, Agent, or Firm*—Sughrue Mion, PLLC

(57) ABSTRACT

A veterinary composition comprising at least one keratolytic and cerumenilytic cleaning agent, a at least one bactericide agent, at least one yeast control agent and at least one anti-irritant and anti-pruriginous agent, which is useful for preventing otitis in dogs and cats.

8 Claims, No Drawings

PREPARATION FOR VETERINARY USE

TECHNICAL FIELD

This invention refers to a preparation for veterinary use, and more specifically to a preparation suitable for ear hygiene and for the prevention of otitis in dogs and cats.

STATE OF THE TECHNIQUE

External otitis is one of the main reasons for veterinary visits and, according to different authors, it represents between 10 and 20% of visits to small animal clinics. It is more frequent in dogs than in cats because of the different shape of the ear pavilion and habits such as ear licking in cats.

The importance of otitis lies in its high incidence, in the potential seriousness of a process that initially affects the outer ear but that frequently affects the middle ear, in the ease with which relapses, usually due to incomplete or unsuitable treatment, occur, and its multi-factorial aetiology, because the infection that follows the inflammation is usually due to several types of micro-organism present at the same time, such as bacteria, fungi and mites.

"Ear cleaning" products are well known. As their name implies, they are only cleaning products, and do not consider such important aspects as asepsis in their application, bactericide activity and yeast control (malassezia), and they are not complete formulas that clean, soften wax and remove yeasts and certain pathogens.

The main disadvantages of currently known veterinary ear products are as follows:

a) Most of these currently known ear products are merely acidifying solutions or cerumenilytic solutions.
b) Other known products do not completely remove organic matter and fats and soften wax. Their cerumenilytic activity is not usually successful.
c) They do not control malassezia levels.

DESCRIPTION OF THE INVENTION

The preparation for veterinary use covered by this invention does not have these disadvantages and is essentially characterised in that it includes at least one agent with keratolytic and cerumenilytic properties, at least one agent with bactericide properties, at least one yeast controlling agent and at least one anti-irritant and anti-pruriginous agent.

According to another of the invention's characteristics, the preparation also includes at least one agent that heightens its cerumenilytic power.

According to another of the invention's characteristics, the preparation also includes at least one vegetable extract with antiseptic and cicatrizant properties.

According to another of the invention's characteristics, the preparation also includes at least one deodorant agent.

According to another of the invention's characteristics, the agent with keratolytic and cerumenilytic cleaning properties is lactic acid, salicylic acid or a mixture of both.

According to another of the invention's characteristics, the bactericide agent is *Cetraria islandica* extract.

According to another of the invention's characteristics, the agent that controls yeast is lactic acid, salicylic acid or a mixture of both.

According to another of the invention's characteristics, the anti-irritant and anti-pruriginous agent is a *Cucumis sativus* vegetable extract.

According to another of the invention's characteristics, the agent that reinforces the preparation's cerumenilytic properties is oleic acid.

According to another of the invention's characteristics, the vegetable extract is *Mimosa tenuiflora* extract, *Cetraria islandica* extract, *Camomilla recutica* extract, or a mixture of all three.

According to another of the invention's characteristics, the deodorant agent is *Cetraria islandica* extract.

According to another of the invention's characteristics, it claims a composition based on between 65 and 80% weight of propylene glycol or butylene glycol, or a mixture of both; between 10 and 15% weight of polyethylene glycol 400; between 2 and 10% weight of ethoxydiglycol; between 1 and 5% weight of de-ionised water; between 2 and 5% weight of glycerine or diglycerol, or a mixture of both; between 1 and 4% weight of lactic acid, between 1 and 6% weight of *Cetraria islandica, Mimosa tenuiflora* and/or *Camomilla recutica* extract, or a mixture of both; between 0.1 and 0.5% weight of oleic acid; and between 0.1 and 0.5% weight of salicylic acid.

According to another of the invention's characteristics, its claims the use of the aforementioned preparation for obtaining an otic drug for veterinary purposes.

According to another of the invention's characteristics, it claims a single-dose pharmaceutical presentation consisting of the preparation covered by the invention, for administration as an otic drug for veterinary purposes.

EXAMPLE

To manufacture 1,000 g of the preparation covered by this invention, 711 g of propylene glycol are introduced in a completely clean and disinfected recipient with a mixer, and 30 g of glycerine, 10 g of Cucumis sativus, 5 g of *Cetraria islandica* and 5 g of *Mimosa tenuiflora* are gradually added.

In a separate container, 2.2 g of salicylic acid, 50 g of ethoxydiglycol and 2.5 g of oleic acid are mixed. This mixed is added to the above, and mixed in the recipient. 30 g of sterile de-ionised water and 29.3 g of lactic acid are mixed and added to the above, continuing to mix. Finally, continuing to mix, 125 g of polyethylene glycol 400 are added.

Following is a description of an alternative production process, in which the same product quantities are used. The propylene glycol is introduced into the clean and disinfected recipient, with a mixer, and the glycerine and the vegetable extracts are gradually added.

In another container, the salicylic acid is dissolved by mixing in the ethoxydiglycol. When a perfect solution has been obtained, the oleic acid is added and the mixture is added to the above and mixed.

In another container, the mixture of polyethylene glycol 400, water and lactic acid is prepared, in this order. Once the mixture is homogeneous, it is added to and mixed with the above. Mixing continues for a few minutes and then the product is ready.

To pack the product obtained with either of the two processes, it is filtered through fine nylon muslin and packed in single-dose bottles using the "blow fill and seal in bottle pack" method, which gives the product differential microbiological conditions (Pharmacopoeia Europea type II).

Packing the product in single-dose hermetically sealed bottles considerably improves the storage conditions and the hygienic administration of the product.

Following is a study conducted with the preparation covered by the invention, which values its cleaning effect, its irritant potential and its yeast control properties, showing a high level of efficacy.

Test to Assess the Cleaning Effect, the Irritant Potential and the Yeast Control Effect of the Preparation Described in the Example A total number of 20 dogs (12 males and 8 females) of between 4 and 8 years of age were used. 18 were beagles and the other two were mongrels, chosen at random from a group of dogs at the Veterinary Faculty of the Universidad Autónoma de Barcelona.

The study was designed so that each animal was its own control. The product was only applied in the right auditory canal of each of the animals, so that the animals' left auditory canal was a negative control.

The product was applied for a total of 30 days. For the first 15 days, between 2 and 3 ml of product was applied once a day, and during the next 15 days, the same amount was applied every two days. Nothing was applied to the left auditory canal.

A total of 3 verification visits were made during the study.

VISIT 1: the day before the product was applied

VISIT 2: when the product had been applied daily for 15 days

VISIT 3: when the product had been applied daily for 15 days and on alternate days for 15 days.

The following operations were performed on each of these visits:

Superficial otological examination of the auditory conduct in each animal's two ears to assess the amount of wax and secretions. This amount was assessed by means of an ordinal scale including the following categories: Absent, Slight, Moderate and Intense. The type of secretion observed was also specified.

otological examination using an otoscope of both conducts, to assess the level of irritation. This level was assessed by means of an ordinal scale including the following categories: Absent, Slight, Moderate and Intense.

Collection of samples from both auditory canals, for a cytological study based on the determination of the number of malassezias per 40 degree field.

Results

A prior analysis of the results shows the baseline homogeneousness between each animal's two auditory canals related to the level of a) wax and secretions and b) irritation, and related to the number of Malassezias in the samples taken from each of the two canals.

Level of wax and secretions

The level of wax and secretions observed in each of the animal's two auditory canals at the start of the study was very homogeneous. 19 of the 20 animals presented the same level of wax and secretions in both auditory canals; 8 of these animals had no wax or secretions in either of the two canals, whereas 5 had a slight level of wax and secretions, 2 had a moderate level and 4 had an intense level in both canals. Only one of the 20 animals had a slight level in the right auditory canal with no wax or secretions in the left canal (table 1).

Table 1, Baseline homogeneousness between the right auditory canals (RAC) and the left auditory canals (LAC) of each animal in relation to the level of wax and secretions observed during visit 1 (expressed as number of animals). In bold, the animals with homogeneous values between both canals.

|     |          | LAC    |        |          |         |       |
|-----|----------|--------|--------|----------|---------|-------|
|     |          | Absent | Slight | Moderate | Intense | TOTAL |
| RAC | Absent   | 8  | 0      | 0        | 0       | 8     |
|     | Slight   | 1      | 5  | 0        | 0       | 6     |
|     | Moderate | 0      | 0      | 2    | 0       | 2     |
|     | Intense  | 0      | 0      | 0        | 4   | 4     |
|     | TOTAL    | 9      | 5      | 2        | 4       | 20    |

In the cases with secretion, the type of secretion was dark brown with a texture between dense and liquid.

Level of Irritation

The level of irritation observed in each animal's two auditory canals at the start of the study was very homogeneous. All the animals presented the same level of irritation in both auditory canals; 12 of the animals had no irritation in either of the two canals, whereas 6 animals had a slight level of irritation and 2 had a moderate level in both canals (table 2).

Table 2, Baseline homogeneousness between the right (RAC) and left (LAC) auditory canal of each animal related to the level of irritation observed in visit 1 (expressed as a number of animals). In bold, the animals with homogeneous values between both canals.

|     |          | LAC    |        |          |         |       |
|-----|----------|--------|--------|----------|---------|-------|
|     |          | Absent | Slight | Moderate | Intense | TOTAL |
| RAC | Absent   | 12 | 0      | 0        | 0       | 12    |
|     | Slight   | 0      | 6  | 0        | 0       | 6     |
|     | Moderate | 0      | 0      | 2    | 0       | 2     |
|     | Intense  | 0      | 0      | 0        | 0   | 0     |
|     | TOTAL    | 12     | 6      | 2        | 0       | 20    |

Number of Malassezia/40 Degree Field

In this case, since this is a continuous variant, we calculated the mean of the counts from samples taken from the right auditory canal and it was compared with the mean of the counts from samples taken from the left auditory canal at the start of the study (visit 1) These mean numbers, and their standard deviations, were very homogeneous (table 3).

Table 3, Baseline values of the number of malassezia per 40 degree field observed during the cytological study of the right (RAC) and left (LAC) auditory canals.

|     | Average | S.D.  | Mean | Min | Max |
|-----|---------|-------|------|-----|-----|
| RAC | 19.6    | 31.95 | 5    | 0   | 95  |
| LAC | 19.6    | 32.79 | 6    | 0   | 100 |

Assessment of the Cleaning Effect

The cleaning effect was assessed according to the evolution of the level of wax and secretions between visits 1 and 2 and between visits 1 and 3, A numerical variable was assigned to each of the values on the ordinal scale, as follows: Absent=0, Slight=1, Moderate=2 and Intense=3.

The difference between the value on visit 2 or visit 3 and the value on visit 1 in each case gave a number that varied between −3 (maximum reduction in the level of wax and secretions) and 3 (maximum worsening), going through 0 (no change in the level).

Table 4 describes the parallel evolution of the level of wax and secretions observed between visit 1 and visit 2 in the right (RAC) and left (LAC) auditory canals (expressed in the aforementioned reduction or increase values). The values indicate the number of animals with concrete rates of improvement in the right and left auditory canals.

TABLE 4

|  |  | LAC (Control) | | | | | | | |
|  |  | Improvement | | | | Worsening | | | |
|  |  | -3 | -2 | -1 | 0 | +1 | +2 | +3 | TOTAL |
|---|---|---|---|---|---|---|---|---|---|
| RAC Improvement (Treat) | -3 | ■ | - | - | - | - | - | - | 0 |
|  | -2 | - | ■ | 1 | 2 | - | - | - | 3 |
|  | -1 | - | - | ■ | 2 | - | - | - | 3 |
|  | 0 | - | - | - | ■ | 4 | 2 | - | 8 |
|  | +1 | - | - | - | - | ■ | 3 | - | 6 |
|  | +2 | - | - | - | - | - | ■ | - | 0 |
| Worsening | +3 | - | - | - | - | - | - | ■ | 0 |
|  | TOTAL | 0 | 0 | 2 | 6 | 7 | 5 | 0 | 20 |

The values in the shaded boxes are equivalent to the animals in which both auditory canals (right and left) evolved in the same way. As can be seen, the other animals are above the diagonal formed by the shaded boxes, indicating that the evolution of the right auditory canals, where the product was applied, was better than the evolution of the left auditory canals in the same animals.

The analysis of these values using the Wilcoxon test for data pairs showed that the evolution of the level of wax and secretions between visits 1 and 2 was significantly better in the auditory canals to which the product was applied (Z=3.53; p=0.0004).

Table 5 shows the parallel evolution of the level of wax and secretions observed between visit 1 and visit 3 in t he right (RAC) and left (LAC) auditory canals (expressed in the aforementioned reduction and increase values).

TABLE 5

|  |  | LAC (Control) | | | | | | | |
|  |  | Improvement | | | | Worsening | | | |
|  |  | -3 | -2 | -1 | 0 | +1 | +2 | +3 | TOTAL |
|---|---|---|---|---|---|---|---|---|---|
| RAC Improvement (Treat) | -3 | ■ | - | 1 | - | - | - | - | 1 |
|  | -2 | - | ■ | - | 2 | - | - | - | 2 |
|  | -1 | - | - | ■ | 2 | 2 | - | - | 5 |
|  | 0 | - | - | - | ■ | 6 | 2 | - | 9 |
|  | +1 | - | - | - | - | ■ | - | 1 | 3 |
|  | +2 | - | - | - | - | - | ■ | - | 0 |
| Worsening | +3 | - | - | - | - | - | - | ■ | 0 |
|  | TOTAL | 0 | 0 | 2 | 5 | 10 | 2 | 1 | 20 |

As observed on table 4, most of the animals are above that diagonal formed by the shaded boxes, indicating that the evolution of the right auditory canals, where the product was applied, was better than the evolution of the same animals' left auditory canals.

The analysis of these values by the Wilson text for data pairs showed that the evolution of the level of wax and secretions between visits 1 and 3 was significantly better for the auditory canals to which the product was applied (Z=3.73; p=0.0002). It is worth mentioning that for the animals that on visits 2 and 3 presented some level of secretion the right ear, it was described as clean and a bright white colour, unlike on the first visit, when it was described as dark brown. This happened in 12 of the animals during treatment, in 3 of which this white secretion disappeared completely when the frequency with which the product was applied was reduced and in the rest soon after the end of the study.

The subjective assessment of the cleaning effect, made by the veterinary surgeon on visits 2 and 3 was classified on a scale of values that included Insufficient, Discreet, Good and Excellent. The results were as follows:

|  | Excellent | Good | Discreet | Insufficient |
|---|---|---|---|---|
| VISIT 2 | 1 | 13 | 6 | 0 |
| VISIT 3 | 1 | 18 | 1 | 0 |

Assessment of the irritant potential

The assessment of the irritant potential was based on the evolution of the level of irritation between visits 1 and 2 and visits 1 and 3, As for the cleaning effect (section 9.2) a numerical variable was assigned to each of the values on the ordinal scale, as follows: Absent=0, Slight=1, Moderate=2, Intense=3, The difference between the value on visit 2 or visit 3 and the value on visit 1 in each case resulted in a number that could vary between −3 (maximum reduction of the level of irritation) and 3 (maximum worsening), going through 0 (no change of level).

Table 6 describes the parallel evolution of the level of irritation observed between visit 1 and visit 2 in the right (RAC) and left (LAC) auditory canals (expressed in the aforementioned reduction or increase values). The values in the boxes indicate the number of animals with concrete rates of worsening in the right and left auditory canals.

TABLE 6

|  |  | LAC (Control) | | | | | | | |
|  |  | Improvement | | | | Worsening | | | |
|  |  | -3 | -2 | -1 | 0 | +1 | +2 | +3 | TOTAL |
|---|---|---|---|---|---|---|---|---|---|
| RAC Improvement (Treat) | -3 | ■ | - | - | - | - | - | - | 0 |
|  | -2 | - | ■ | 1 | - | - | - | - | 1 |
|  | -1 | - | - | ■ | 4 | 2 | - | - | 6 |
|  | 0 | - | - | - | ■ | 3 | 3 | - | 13 |
|  | +1 | - | - | - | - | ■ | - | - | 0 |
|  | +2 | - | - | - | - | - | ■ | - | 0 |
| Worsening | +3 | - | - | - | - | - | - | ■ | 0 |
|  | TOTAL | 0 | 0 | 1 | 11 | 5 | 3 | 0 | 20 |

The values in the shaded boxes represent the animals in which both auditory canals (right and left) evolved in the same way. As can be seen, the rest of the animals are above the diagonal formed by the shaded boxes, indicating that the evolution of the right auditory canals, to which the product was applied, was better than the evolution of the left auditory canals in the same animals.

The analysis of these values by the Wilcoxon test for data pairs showed that the evolution of the level of irritation between visits 1 and 2 was significantly better in the auditory canals to which the product was applied (Z=3.40; p=0.0007).

Table 7 describes the parallel evolution of the level of irritation observed between visit 1 and visit 3 in the right (RAC) and left (LAC) auditory canals (expressed in the aforementioned reduction or increase values).

TABLE 7

|  |  | LAC (Control) | | | | | | | |
|---|---|---|---|---|---|---|---|---|---|
|  |  | Improvement | | | | Worsening | | | |
|  |  | -3 | -2 | -1 | 0 | +1 | +2 | +3 | TOTAL |
| RAC Improvement (Treat) | -3 | ■ | - | - | - | - | - | - | 0 |
|  | -2 | - | ■ | - | - | 2 | - | - | 2 |
|  | -1 | - | - | ■ | 3 | 1 | 1 | - | 5 |
|  | 0 | - | - | - | ■ | 5 | 3 | 1 | 12 |
|  | +1 | - | - | - | - | ■ | 1 | - | 1 |
|  | +2 | - | - | - | - | - | ■ | - | 0 |
| Worsening | +3 | - | - | - | - | - | - | ■ | 0 |
|  | TOTAL | 0 | 0 | 0 | 6 | 8 | 5 | 1 | 20 |

As seen on table 6, most of the animals are above the diagonal formed by the shaded boxes, indicating that the evolution of the right auditory canals, to which the product was applied, was better than the evolution of the left auditory canals in the same animals.

The analysis of these values by the Wilcoxon test for data pairs showed that the evolution of the level of irritation between visits 1 and 3 was significantly better in the auditory canals to which the product was applied (Z=3.81; p=0.0001).

Assessment of the yeast control effect

Table 8 shows the averages and standard deviations of the differences between the number of malassezia observed between visit 1 and visit 2 in each of the two auditory canals of each animal.

TABLE 8

|  | Average | S.D. | Mean | Min | Max |
|---|---|---|---|---|---|
| RAC | -11.2 | 25.79 | -3 | -86 | 29 |
| LAC | 2.9 | 22.26 | -0.5 | -65 | 50 |

The results indicate that there was a reduction in the number of malassezia in the right auditory canal, where the product was applied, whereas there was a slight increase in the fungi in the left auditory canal.

The analysis of these values by means of Student's T-test showed that the differences observed between visits 1 and 2 are statistically significant (t=2.34; p=0.0302).

Finally, table 9 shows the averages and standard deviations of the differences between the number of malassezia observed between visit 1 and visit 3 in each of the auditory canals of each animal.

TABLE 9

|  | Average | S.D. | Mean | Min | Max |
|---|---|---|---|---|---|
| RAC | -10.4 | 27.02 | -2.5 | -88 | 34 |
| LAC | 7 | 13.05 | 5.5 | -10 | 54 |

The results indicate that there was a reduction in the number of malassezia in the right auditory canal, where the product was applied, whereas there was a slight increase in the fungi in the left auditory canal.

The analysis of these values by means of Student's T-test showed that the differences observed between visits 1 and 3 are statistically significant (t=3.15; p=0.0053).

Conclusions

Based on the results obtained from this study, the following conclusions can be reached:

$1^{st}$. The preparation covered by this invention, applied with the pattern used in this study, presents an excellent cleaning effect, removing the wax and secretions from the dog's auditory canal, and therefore reducing one of the most important factors involved in the appearance of otitis in this species.

$2^{nd}$. This preparation has no irritant potential, and even helps to reduce existing irritation, probably indirectly by reducing the wax and secretions in the auditory canal.

$3^{rd}$. The results obtained after 15 days of daily administration (visit 2) show an excellent cleaning effect. The effect observed after a further 15 days of administration on alternate days (visit 3) is not much greater. This may be relevant if a shorter time of application is required. Nevertheless, during the subjective assessment by the researcher, in 5 out of 6 cases in which the cleaning effect was defined as discreet during visit 2, this effect was classified as Good on visit 3, showing the beneficial effect of continuing treatment for a further 15 days.

Additional Examples

Other composition like the following were also prepared and tested:

| Composition 2: | |
|---|---|
| Butylene glycol | 720 g |
| Polyethylene glycol | 125 g |
| Ethoxydiglycol | 50 g |
| De-ionised water | 25 g |
| Glycerine | 31 g |
| Lactic acid | 20.3 g |
| *Cucumis sativus* | 8 g |
| *Cetraria islandica* | 8 g |
| *Mimosa tenuiflora* | 8 g |
| Oleic acid | 2.5 g |
| Salicylic acid | 2.2 g |
| Composition 3: | |
| Propylene glycol | 707.3 g |
| Polyethylene glycol | 125 g |
| Ethoxydiglycol | 50 g |
| De-ionised water | 30 g |
| Diglycerol | 28 g |
| Lactic acid | 25 g |
| *Cucumis sativus* | 10 g |
| *Cetraria islandica* | 10 g |
| *Camomilla recutica* | 10 g |
| Oleic acid | 2.5 g |
| Salicylic acid | 2.2 g |

What is claimed is:

1. A veterinary composition comprising at least one keratolytic ad cerumenilytic cleaning agent, wherein said keratolytic and cerumenilytic cleaning agent in lactic acid, salicylic acid or a mixture thereof; at least one bactericide agent, wherein said bactericide agent is a *Cetraria islandica* extract; at least one yeast control agent wherein said yeast control agent in lactic acid, salicylic acid or a mixture thereof; and at Least one anti-irritant an anti-pruriginous agent, wherein said anti-irritant and anti-pruriginous agent is a *Cucumis sativus* vegetable extract.

2. The composition accord to claim 1, further comprising at least one agent that heightens carumanilytic properties of said composition.

3. The composition according to claim 1, further comprising at least one vegetable extract with antiseptic and cicatrizant properties, wherein said vegetable extract is a *Mimosa tenuiflora* extract, *Cetraria islandica* extract, *Camomilla recutica* extract or a mixture thereof.

4. The composition according to claim 1, further comprising at least one deodorant, wherein said deodorant is a *Cetraria islandica* extract.

5. The composition according to claim 2, wherein said agent that heightens the cerumenilytic properties of said composition is oleic acid.

6. The composition according to claim 1, wherein said composition comprises, based on the total weight of the composition, between 65 and 80% by weight of propylene glycol, butylene glycol or a mixture thereof; between 10 and 15% by weight of polyethylene glycol 400; between 2 and 10% by weight of ethoxydiglycol; between 1 and 5% by weight of de-ionised water; between 2 and 5% by weight of glycerine or diglycerol, or a mixture thereof; between 1 and 4% by weight of lactic acid; between 1 and 6% by weight of a *Cucumis sativus* extract, between 1 and 6% by weight of a *Cetraria islandica* extract, *Mimosa tenuiflora* extract, *Camomilla recutica* extract, or a mixture thereof; between 0.1 and 0.5% by weight of oleic acid; and between 0.1 and 0.5% by weight of salicylic acid.

7. A single dose pharmaceutical product useful as a veterinary otic drug comprising the composition according to claim 1.

8. A method for treating otitis in a veterinary animal comprising administering to the ear of a veterinary animal, the composition according to claim 1.

* * * * *

UNITED STATES PATENT AND TRADEMARK OFFICE
CERTIFICATE OF CORRECTION

PATENT NO. : 6,793,932 B2
DATED : September 21, 2004
INVENTOR(S) : Antonio Lopez Cabrera and Josep Homedes Beguer It is certified that error appears in the above-identified patent and that said Letters Patent is hereby corrected as shown below:

<u>Title page,</u>
Item [73], Assignee, "Laboratories Del Dr. Esteve, S.A." should read
-- Laboratorios Del Dr. Esteve, S.A. --

Signed and Sealed this

Twenty-ninth Day of March, 2005

JON W. DUDAS
*Director of the United States Patent and Trademark Office*